(12) United States Patent
Iwai et al.

(10) Patent No.: US 6,786,101 B2
(45) Date of Patent: Sep. 7, 2004

(54) WELD STRENGTH DETERMINATION METHOD, CASING STRUCTURE, CASING STRUCTURE FOR IMAGE FORMING APPARATUS, AND WELD STRENGTH DETERMINATION METHOD IN CASING FOR IMAGE FORMING APPARATUS

(75) Inventors: Koji Iwai, Ibaraki (JP); Tsuneo Ohashi, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/159,131

(22) Filed: Jun. 3, 2002

(65) Prior Publication Data
US 2002/0194931 A1 Dec. 26, 2002

(30) Foreign Application Priority Data

Jun. 7, 2001 (JP) .......................... 2001-172601
Apr. 19, 2002 (JP) .......................... 2002-118000

(51) Int. Cl.$^7$ ................................ G01N 3/20
(52) U.S. Cl. ................................................ 73/850
(58) Field of Search .................... 73/37, 850, 800; 219/61, 121.64, 130.01, 124.34, 130.21, 121.63; 228/103; 524/115, 404, 449; 428/615; 356/33, 367; 53/281; 700/212; 29/897.2; 52/788.1

(56) References Cited

U.S. PATENT DOCUMENTS

| 4,649,256 | A | * | 3/1987 | Minamida et al. ..... 219/121 LD |
| 4,789,236 | A | * | 12/1988 | Hodor et al. ................. 356/33 |
| 4,920,249 | A | * | 4/1990 | McLaughlin et al. .. 219/130.21 |
| 5,040,125 | A | * | 8/1991 | Okumura et al. ........... 364/477 |
| 5,585,921 | A | * | 12/1996 | Pepper et al. ............... 356/357 |
| 5,628,518 | A | * | 5/1997 | Ushio et al. ................. 277/180 |
| 5,749,201 | A | * | 5/1998 | Cochrane ...................... 53/281 |
| 6,350,533 | B1 | * | 2/2002 | Goto et al. .................. 428/615 |
| 6,455,803 | B1 | * | 9/2002 | Fields, Jr. et al. ...... 219/121.63 |

FOREIGN PATENT DOCUMENTS

| JP | 9-47873 | 2/1997 |
| JP | 11-135956 | 5/1999 |
| JP | 11-346065 | 12/1999 |

* cited by examiner

*Primary Examiner*—Edward Lefkowitz
*Assistant Examiner*—Octavia Davis
(74) *Attorney, Agent, or Firm*—Fitzpatrick, Cella, Harper & Scinto (57) ABSTRACT

This invention has as its object to facilitate determination of a weld strength of welded target members when a plurality of metal members are welded. In order to achieve this object, when a plurality of metal members are welded, a weld strength of the welded target members is determined on the basis of the state of a lower bead.

4 Claims, 9 Drawing Sheets

WELD STRENGTH DETERMINATION METHOD, CASING STRUCTURE, CASING STRUCTURE FOR IMAGE FORMING APPARATUS, AND WELD STRENGTH DETERMINATION METHOD IN CASING FOR IMAGE FORMING APPARATUS

FIELD OF THE INVENTION

The present invention relates to a metal member welding technique and, more particularly, to a weld strength guaranteeing technique for a welded metal plate.

The present invention also relates to a strength guarantee determination technique in a casing structure for an image forming apparatus.

BACKGROUND OF THE INVENTION

As a technique of overlaying base materials and welding them, those as disclosed in Japanese Patent Laid-Open No. 9-47873 are known.

Welding techniques for a casing structure for an image forming apparatus such as a copying machine or laser beam printer are disclosed in Japanese Patent Laid-Open Nos. 11-135956 and 11-346065.

Regarding a device casing structure for an industrial product such as an office machine, e.g., an image forming apparatus, or an industrial machine, sometimes the structure has a complicated shape or an odd shape other than a square or rectangular shape.

In such a casing structure, sometimes the structure is formed by welding a plurality of metal plates, and the mechanical strength of the structure is therefore guaranteed.

In strength guarantee for a welded portion of metal plates, the welding conditions are set considering various factors such as the thicknesses of the metal plates to be welded, welding means, the necessary design strength of a casing structure to be welded. The casing welded on the basis of the preset welding conditions is subjected to a strength test to obtain optimal conditions. Strength guarantee is performed with the optimal conditions. Due to factors such as variations in size of the metal plates and a change in conditions of the welding means, sometimes the strength of the welded casing is not sufficiently guaranteed for.

At the manufacturing site of the casing structure, the welding conditions are altered to correspond to a change in various types of manufacturing states, e.g., alteration of the welding conditions due to a change in the type of the metal members to be welded or in thicknesses of the members. Each time the welding conditions are altered, a test must be performed to guarantee the strength of the welded casing. When the welding conditions are altered often, checking the strength guarantee adversely affects productivity.

SUMMARY OF THE INVENTION

The present invention has been made in view of the above problem, and has as its object to facilitate determination of the weld strength of welded target bonding members when a plurality of metal members are welded.

In order to solve the above problem and to achieve the above object, a weld strength determination method according to the present invention is characterized by the following process.

More specifically, when a plurality of metal members are welded, a weld strength of welded target members is determined on the basis of the state of a lower bead.

According to the first aspect of the present invention, a casing structure for an image forming apparatus is characterized by the following arrangement.

More specifically, according to the present invention, there is provided a casing structure for an image forming apparatus, which has a casing formed by welding a plurality of metal plates, wherein a length of a lower bead of a welded portion of the welded casing structure is set to not less than a predetermined length, so a strength of the casing structure is guaranteed for.

According to the second aspect of the present invention, a casing structure for an image forming apparatus is characterized by the following arrangement.

More specifically, the casing structure comprises a frame member for placing an original unit and an optical unit thereon, and a plurality of side plate members, a bottom plate member, and a front plate member to be fixed to the frame member, wherein the frame member and the plurality of side plate members, the bottom plate member, and the front plate member are partially overlaid and welded with a laser to form a three-dimensional structure.

A weld strength determination method in an image forming apparatus according to the present invention is characterized by the following process.

More specifically, there is provided a weld strength determination method in a casing for an image forming apparatus which comprises a frame member for placing an original unit and an optical unit thereon, and a plurality of side plate members, a bottom plate member, and a front plate member to be fixed to the frame member, and in which the frame member and the plurality of side plate members, the bottom plate member, and the front plate member are partially overlaid and welded with a laser, characterized in that a weld strength is determined on the basis of a size of a weldline appearing on a lower surface of a portion which is welded with the laser.

A casing structure according to the present invention is characterized by the following arrangement.

More specifically, there is provided a casing structure in which a casing is formed by three-dimensionally combining and coupling a plurality of metal members and which comprises a board member and a plurality of plate members to be coupled to the board member, wherein the board member and the plurality of plate members are partially overlaid and welded with a laser, and a ratio of a length of an upper bead to a length of a lower bead of a portion which is welded with the laser is set to not less than a predetermined value.

Other objects, features and advantages of the present invention besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

DETAILED DESCRIPTION OF THE PREFERRED EMBODIMENT

A preferred embodiment of the present invention will be described in detail with reference to the accompanying drawings.

Figure 1:
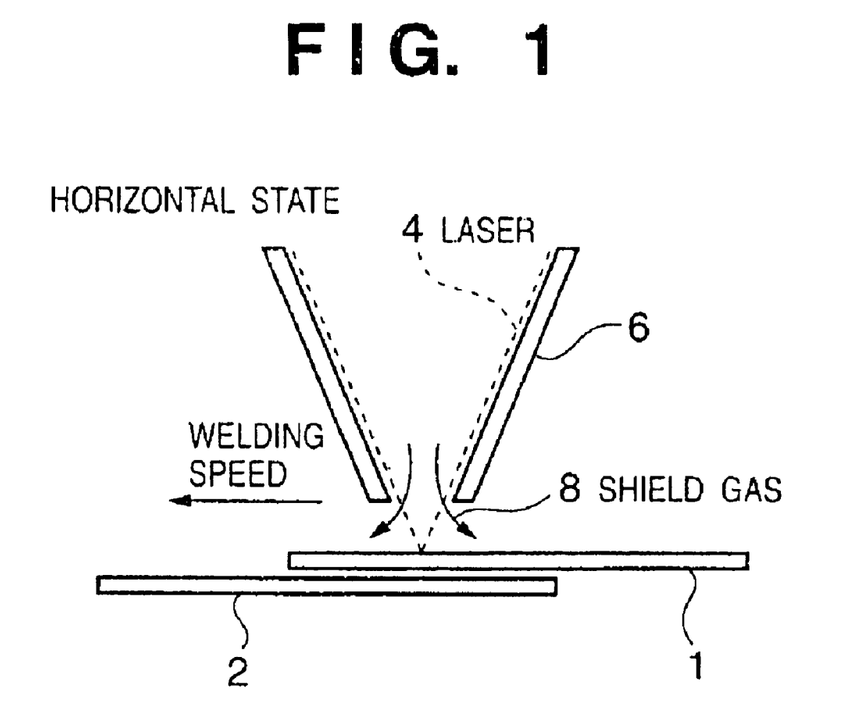
FIG. 1 is a view for explaining welding according to one embodiment of the present invention.

FIG. 1 is a view for explaining a welding state when a plurality of metal plates are to be welded with a laser beam source.

Referring to FIG. 1, reference numerals 1 and 2 denote metal plates to be welded. In this case, the metal plates 1 and 2 are steel sheets with galvanized surfaces.

Reference numeral 4 denotes a laser beam from a laser beam source (not shown); and 6, a shielding member for preventing diffusion of the laser beam 4. A shield gas 8 is injected inside the shielding member 6.

Figure 2:
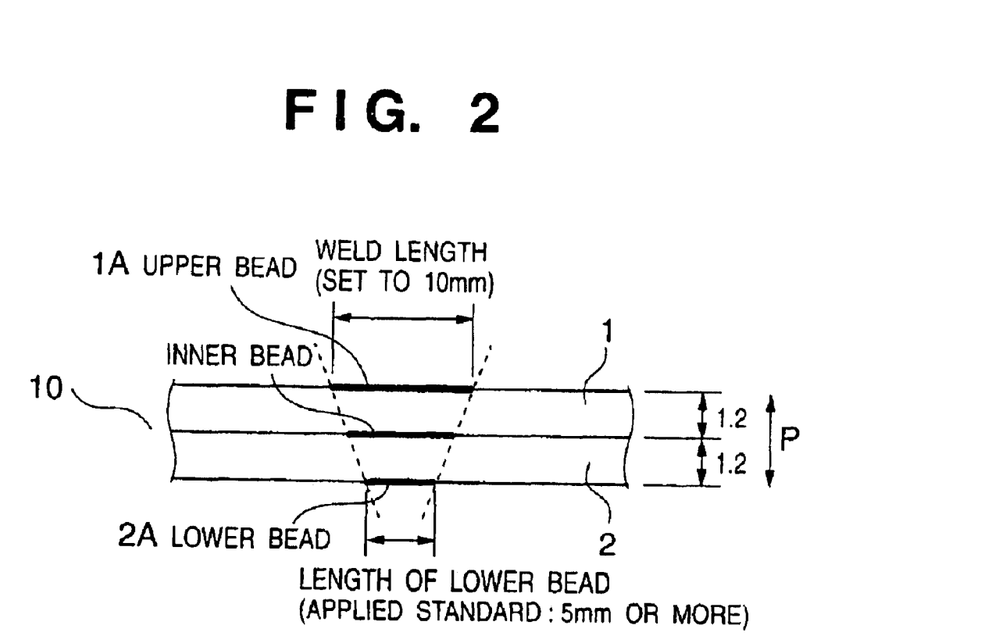
FIG. 2 is a view for explaining welding according to one embodiment of the present invention.

FIG. 2 is a view for explaining the welding operation of the metal plates 1 and 2 to be welded. The galvanized steel sheets 1 and 2 each have a thickness of 1.2 mm. The welded portion has a length of 10 mm.

A welded casing structure 10 is used as a casing for an image forming apparatus such as a copying machine or laser beam printer. The design standard of the company of the present applicant defines that the casing structure 10 should be designed to guarantee for a strength of 140 kgf or more as a mechanical strength in a pulling direction P.

EXAMPLE 1

By using a carbon dioxide gas ($CO_2$) laser as a welding laser beam source, welding was performed under the following conditions.

| | |
|---|---|
| Material to be welded: | galvanized steel sheet members |
| Thickness of steel sheet: | 1.2 mm |
| Posture for welding: | horizontal |
| Gap size of overlaid portion: | 0 mm |
| Shield gas: | argon gas (Ar) |
| Flow rate of shield gas: | 25 liters/min |
| Laser output: | 2.0 kW |
| Welding speed: | 1.5 m/min |
| Welding direction: | perpendicular (to the pulling direction) |
| Length of welded portion: | 10 mm |

Laser beam irradiation was performed under the above welding conditions. The length of a lower bead 2A as a weldline appearing on the lower side of the second steel sheet 2, with respect to the length (upper bead) 1A of 10 mm of the welded portion on the upper side of the first steel sheet 1, was measured to be 9 mm to 10 mm.

When the welded casing 10 was subjected to a pulling strength test, the pulling strength was 350 kgf to 400 kgf.

This value of the pulling strength test satisfies the specified value described above.

COMPARATIVE EXAMPLE OF EXAMPLE 1

By using a carbon dioxide gas ($CO_2$) laser as a welding laser beam source in the same manner as in Example 1, welding was performed under the following conditions.

| | |
|---|---|
| Material to be welded: | galvanized steel sheets |
| Thickness of steel sheets: | 1.2 mm |
| Posture for welding: | vertical |
| Gap size of overlaid portion: | 0 mm |
| Shield gas: | argon gas |
| Flow rate of shield gas: | 25 liters/min |
| Laser output: | 1.0 kW |
| Welding speed: | 1.5 m/min |
| Welding direction: | perpendicular (to the pulling direction) |
| Length of welded portion: | 10 mm |

The length of a lower bead of the second steel sheet overlaid and welded under the above conditions was 0 mm.

The pulling strength of a casing manufactured in this comparative example was about 10 kgf.

This value falls outside the design conditions described above.

EXAMPLE 2

By using a YAG laser as a welding laser beam source, welding was performed under the following conditions.

| | |
|---|---|
| Material to be welded: | galvanized steel sheets |
| Thickness of steel sheets: | 1.2 mm |
| Posture for welding: | horizontal |
| Gap size of overlaid portion: | 0.2 mm |
| Shield gas: | nitrogen gas ($N_2$) |
| Flow rate of shield gas: | 10 liters/min |
| Laser output: | 1.5 kW |
| Welding speed: | 1 m/min |
| Welding direction: | parallel |
| Length of welded portion: | 10 mm |

In a casing structure welded under the welding conditions of Example 2, the length of a lower bead appearing on the lower side of the second steel sheet 2 was measured to be 9 mm. When the casing structure was subjected to a pulling strength test, the pulling strength was 350 kgf to 400 kgf.

COMPARATIVE EXAMPLE OF EXAMPLE 2

By using a YAG laser as a welding laser beam source in the same manner as in Example 2, welding was performed under the following conditions.

| | |
|---|---|
| Material to be welded: | galvanized steel sheets |
| Thickness of steel sheets: | 1.2 mm |
| Posture for welding: | vertical |
| Gap size of overlaid portion: | 0.2 mm |
| Shield gas: | nitrogen gas |
| Flow rate of shield gas: | 2.5 liters/min |
| Laser output: | 0.7 kW |
| Welding speed: | 1 m/min |
| Welding direction: | parallel |
| Length of welded portion: | 10 mm |

The length of a bead on the lower side of the second steel sheet 2 was measured to be 0 mm. When the casing was subjected to a pulling strength test, the pulling strength was about 10 kgf.

EXAMPLE 3

According to Example 3, the thicknesses of the steel sheets to be overlaid and welded were altered, and the relationship between the lower bead and the mechanical strength was checked.

By using a carbon dioxide gas ($CO_2$) laser as a welding laser beam source, welding was performed under the following conditions.

| | |
|---|---|
| Material to be welded: | galvanized steel sheets |
| Thickness of steel sheets: | 2.0 mm |
| Posture for welding: | horizontal |
| Gap size of overlaid portion: | 0 mm |
| Shield gas: | argon gas (Ar) |
| Flow rate of shield gas: | 25 liters/min |
| Laser output: | 2.0 kW |
| Welding speed: | 1.5 m/min |
| Welding direction: | perpendicular (to the pulling direction) |
| Length of welded portion: | 10 mm |

In a casing welded under the above welding conditions, the length of a bead portion appearing on the lower side of the second steel sheet was measured to be 5 mm. When the casing was subjected to a pulling strength test, the pulling strength was 200 kgf.

COMPARATIVE EXAMPLE OF EXAMPLE 3

By using a carbon dioxide gas ($CO_2$) laser as a welding laser beam source, welding was performed under the following conditions.

| | |
|---|---|
| Material to be welded: | galvanized steel sheet members |
| Thickness of steel sheets: | 2.0 mm |
| Posture for welding: | horizontal |
| Gap size of overlaid portion: | 0 mm |
| Shield gas: | argon gas (Ar) |
| Flow rate of shield gas: | 25 liters/min |
| Laser output: | 1.0 kW |
| Welding speed: | 1.5 m/min |
| Welding direction: | perpendicular (to the pulling direction) |
| Length of welded portion: | 10 mm |

Under the above conditions, the length of a bead appearing on the lower side of the second steel sheet 2 was 0 mm. When the casing structure was subjected to a pulling strength test, the pulling strength was 10 kgf.

EXAMPLE 4

Figure 3:
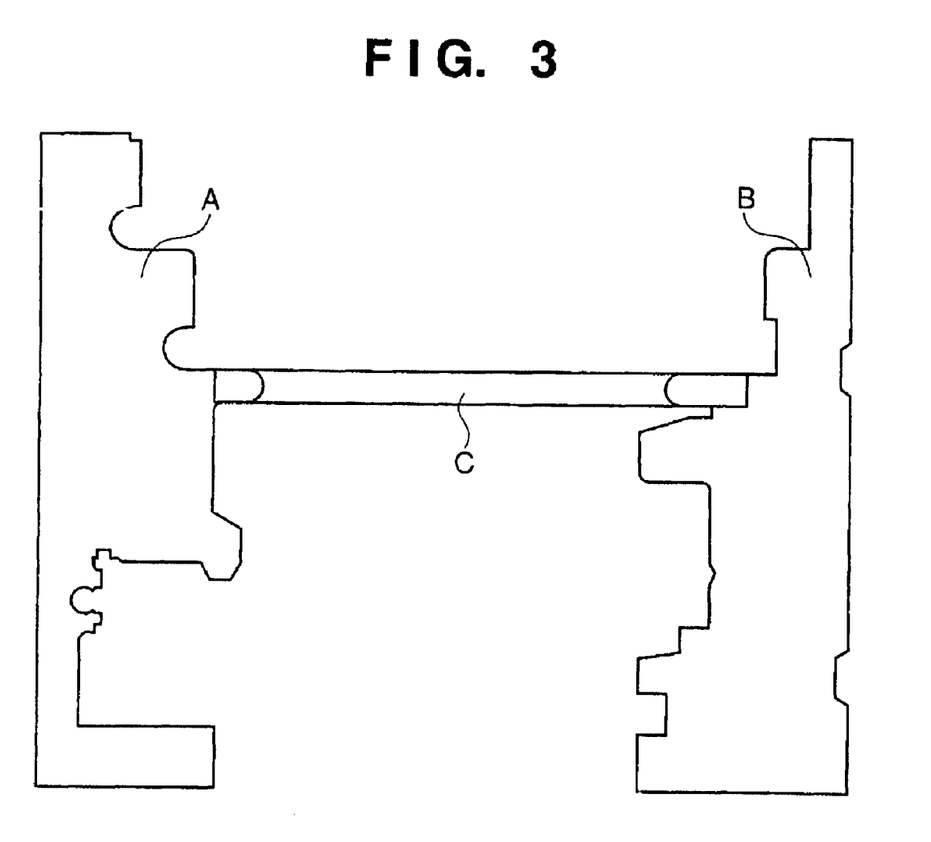
FIG. 3 is a view for explaining a case wherein a welding method according to one embodiment is applied to a casing structure for an image forming apparatus.

In FIG. 3, the present invention is applied to a casing structure for an image forming apparatus (copying machine). FIG. 3 shows the structure of one surface portion of a casing structure portion of a rectangular parallelepiped.

This structure is formed by bonding first and second plate members A and B to a third plate member C by welding.

Figure 4:
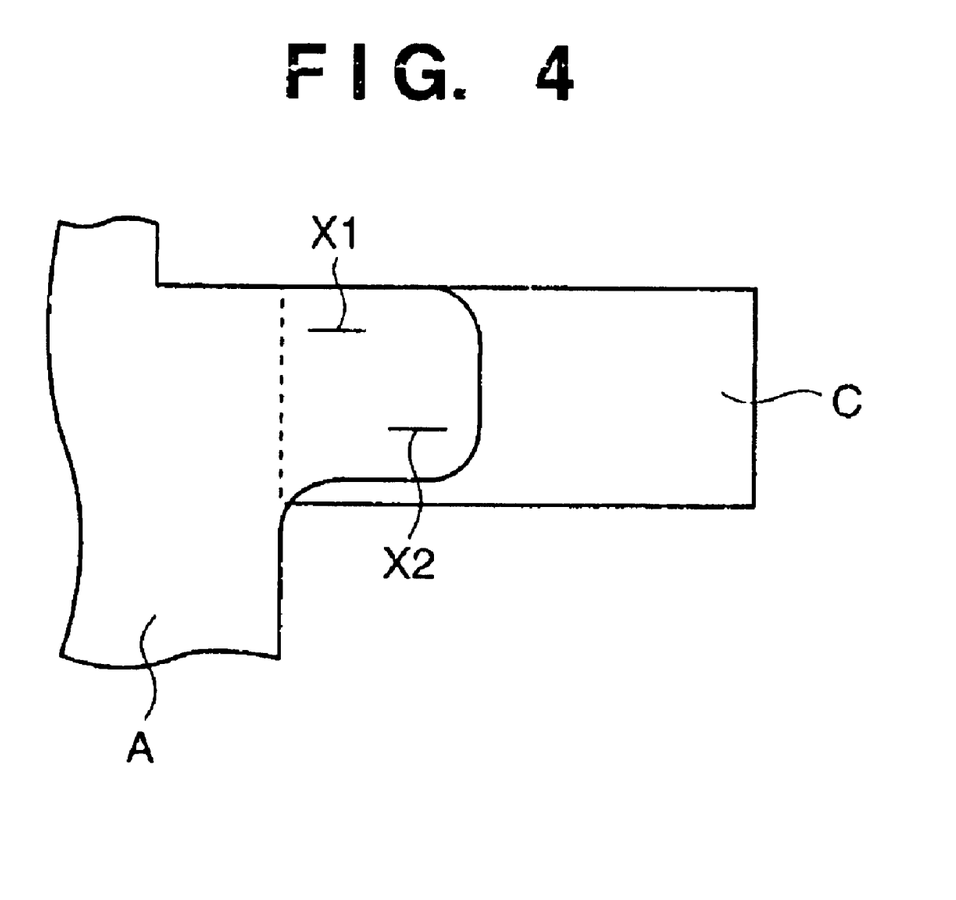
FIG. 4 is a view for explaining a welded portion.

As shown in the enlarged view of FIG. 4, a part of the first plate member A and the left end portion of the third plate member C were overlaid and were welded at portions x1 and x2 in the longitudinal direction of the third plate member C, as shown in FIG. 4.

Figure 5:
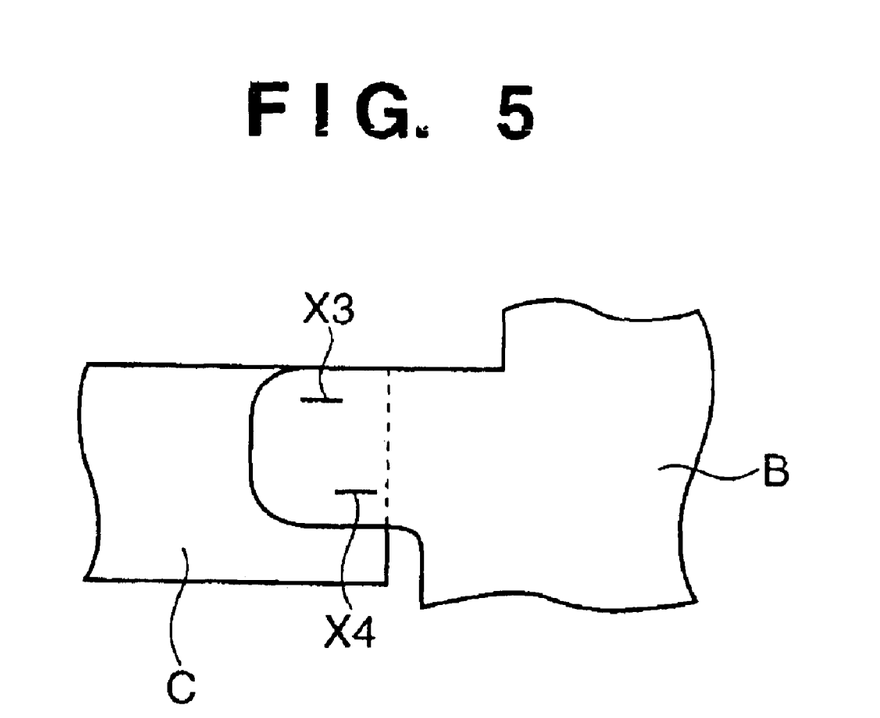
FIG. 5 is a view for explaining a welded portion.

The second and third plate members B and C were also welded at their overlying portions x3 and x4 in the direction of X axis, as shown in FIG. 5.

The lengths of lower beads of the respective welded portions x1, x2, x3, and x4 were set to predetermined lengths or more as described in the above examples. The bonding strength could thus be guaranteed for.

As described above, according to the above embodiment, the mechanical strength of a plurality of metal plates to be overlaid and welded is checked by measuring the length of the lower bead, so frequent alteration in welding conditions can be coped with.

Figure 6:
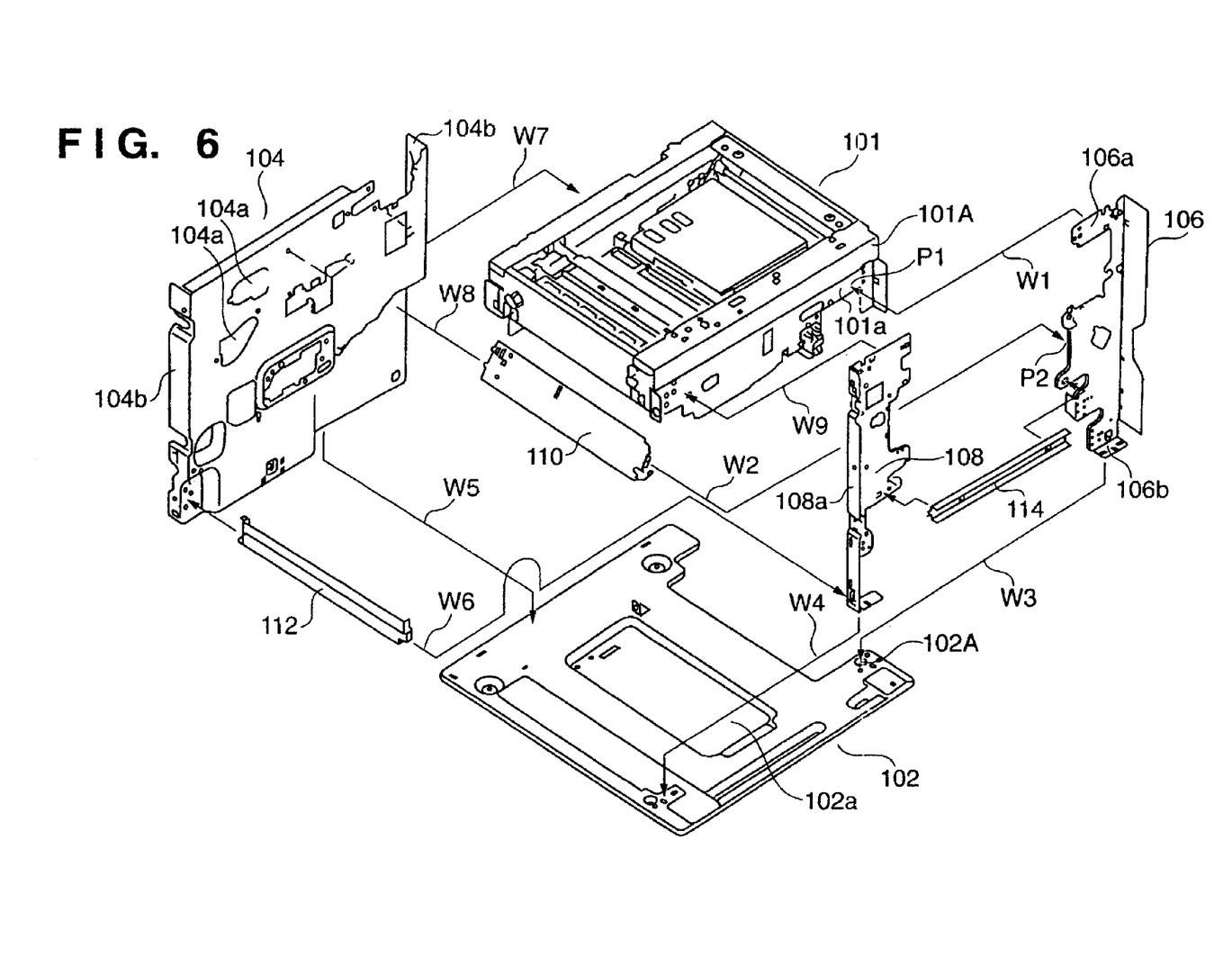
FIG. 6 is an exploded perspective view showing a case wherein the present invention is applied to a casing structure for an image forming apparatus (copying machine)
Figure 7:
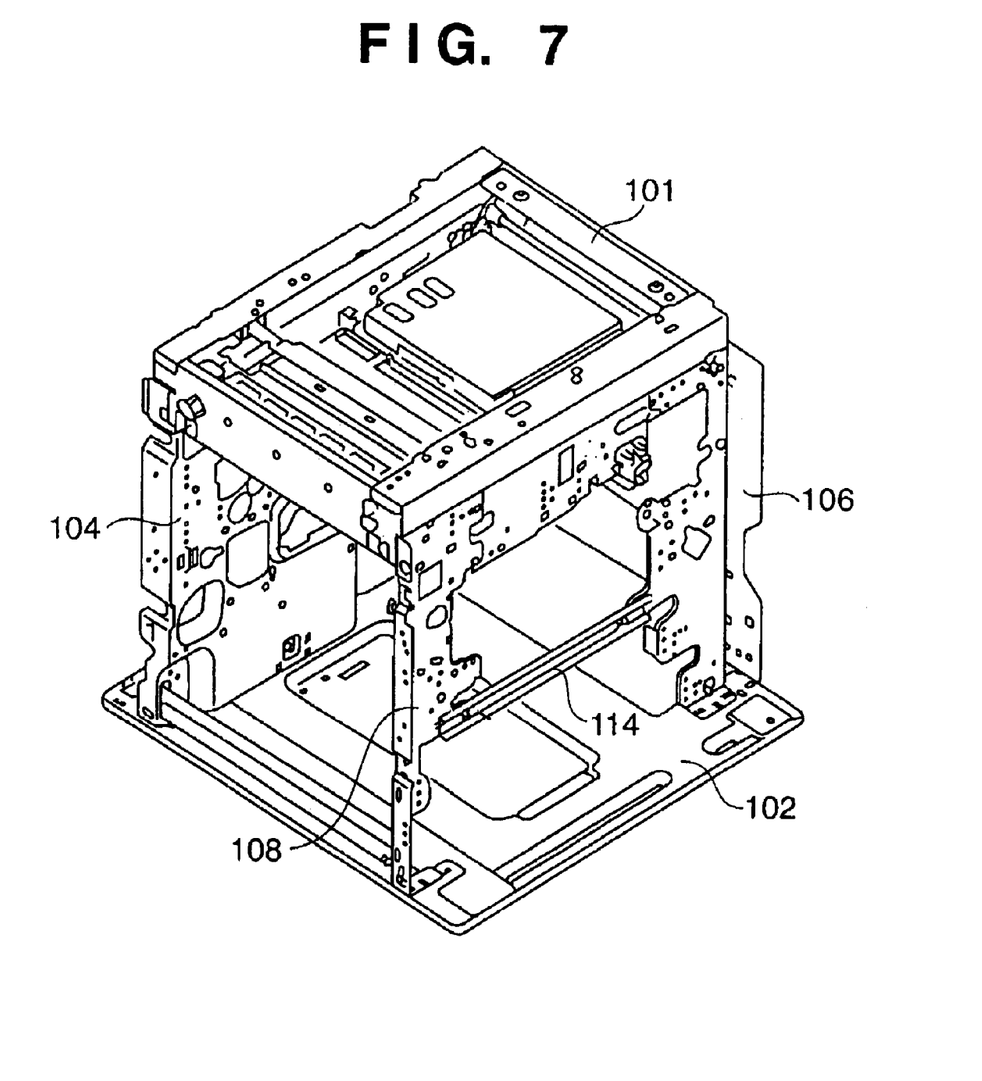
FIG. 7 is a perspective view showing a casing in an assembled state.

FIG. 6 is an exploded perspective view showing a case wherein the present invention is applied to a casing structure for an image forming apparatus (copying machine), and FIG. 7 is a perspective view showing a casing in an assembled state.

Referring to FIG. 6, reference numeral 101 denotes a frame member. The frame member 101 is formed into a box-like shape by combining and press-molding metal steel sheets 101A. An original table unit and an optical unit which illuminates and scans an original are to be placed on the frame member 101. The frame member 101 is formed of galvanized steel sheets, and has a thickness of 1.2 mm.

Reference numeral 102 denotes a bottom plate member of the copying machine. The bottom plate member 102 is a metal plate with a necessary recess 102a formed by pressing. The bottom plate member 102 is formed of a galvanized steel sheet, and has a thickness of 1.2 mm.

Reference numeral 104 denotes a rear plate member of the copying machine. The rear plate member 104 is formed of a galvanized steel sheet, and has a plurality of necessary openings 104a and a plurality of necessary bent portions 104b formed by pressing. The rear plate member 104 has a thickness of 1.2 mm.

Reference numeral 106 denotes a right plate member of a front plate portion to be attached to the frame member 101; and 108, a left plate member of the front plate portion. The right and left plate members 106 and 108 respectively have bent portions 106a and 106b, and a bent portion 108a formed by pressing. Both the right and left plate members 106 and 108 are formed of galvanized steel sheets, and each have a thickness of 1.2 mm.

Reference numeral 110 denotes a stay member for connecting the rear and right plate members 104 and 106; and 112, a stay member for connecting the rear and left plate members 104 and 108.

Reference numeral 114 denotes a convey stay member for holding the right and left plate members 106 and 108.

Each stay member is formed of a galvanized steel sheet, and has a thickness of 1.2 mm.

The frame member 101, the front plate portion (the right and left plate members 106 and 108, and the convey stay member 114), and the like build a three-dimensional casing structure.

Regarding the component arrangement of FIGS. 6 and 7, the respective members are welded with a laser. For example, a bent side surface portion 101a of the frame member 101 and a bent portion 106a of the right plate member 106 are overlaid and welded at a plurality of portions indicated by reference numeral P1, so the frame member 101 and right plate member 106 are joined to each other. The right plate member 106 is welded to the stay member 110 at a portion indicated by reference numeral P2. Also, a lower bent portion 106b of the right plate member 106 is welded to that portion of the bottom plate member 102 which is indicated by reference numeral 102A, so the right plate member 106 is joined to the bottom plate member 102.

Other constituent members are welded in the same manner as described above.

The frame member 101 and the right plate member 106 are laser-welded to each other at the welded portion P1 in the following manner. The right plate member 106 is irradiated with a laser beam from a laser welding means, so an upper bead appears on the upper surface of the right plate member 106 and a lower bead appears on the lower surface of the frame member 101. The laser is YAG laser, and its output is 1.5 kW to 2.0 kW.

The gap of the welded joint of the frame member 101 and right plate member 106 was measured by a gap gauge to be 0 mm to 0.15 mm. The laser scanning distance on the right plate member 106 was 10 mm. The weldline length of the lower bead appearing on the lower side of the frame member 101 was 8 mm to 10 mm.

In this example, the welding operation is performed by setting the laser scanning distance of each portion to 10 mm and the laser output to 1.5 kW to 2 kW. Thus, the length of the lower bead as the lower weldline length was maintained between 8 mm and 10 mm.

With the above conditions and method, a casing in which the respective members build a three-dimensional structure using the frame member as the main component can be obtained. The copying machine is formed with this casing used as the main component.

Respective units constituting the copying machine, e.g., a photosensitive drum unit, a developing unit, a transfer unit, a supply/delivery unit, an original table unit, an electrical circuit unit, and a control panel, are incorporated in this casing, and outer members (not shown) are attached to the front and rear plate portions, thus assembling the copying machine.

Figure 8:
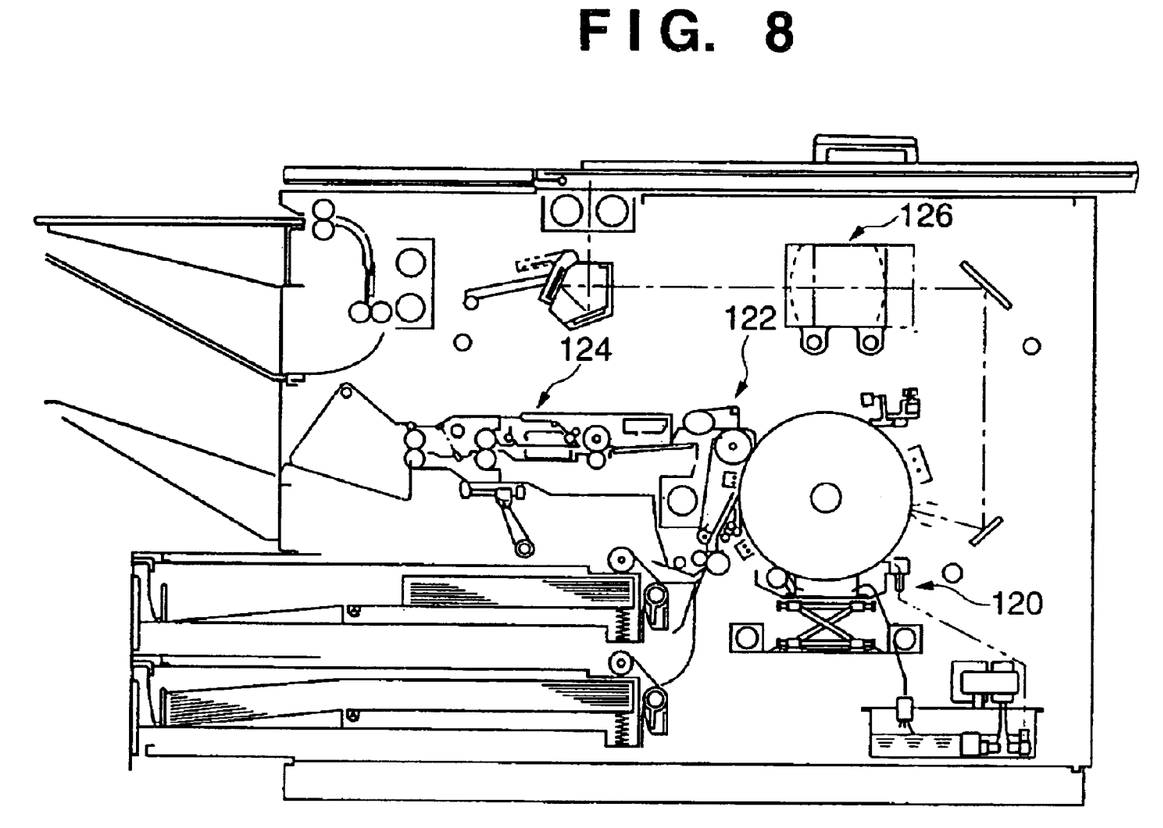
FIG. 8 is a view showing the unit arrangement of a copying machine.

FIG. 8 is a view showing the main constituent units of the copying machine to be incorporated in the casing structure described above.

Referring to FIG. 8, reference numeral 120 denotes a developing unit; 122, a fixing unit; 124, a supply/delivery unit; and 126, an optical unit.

Figure 9:
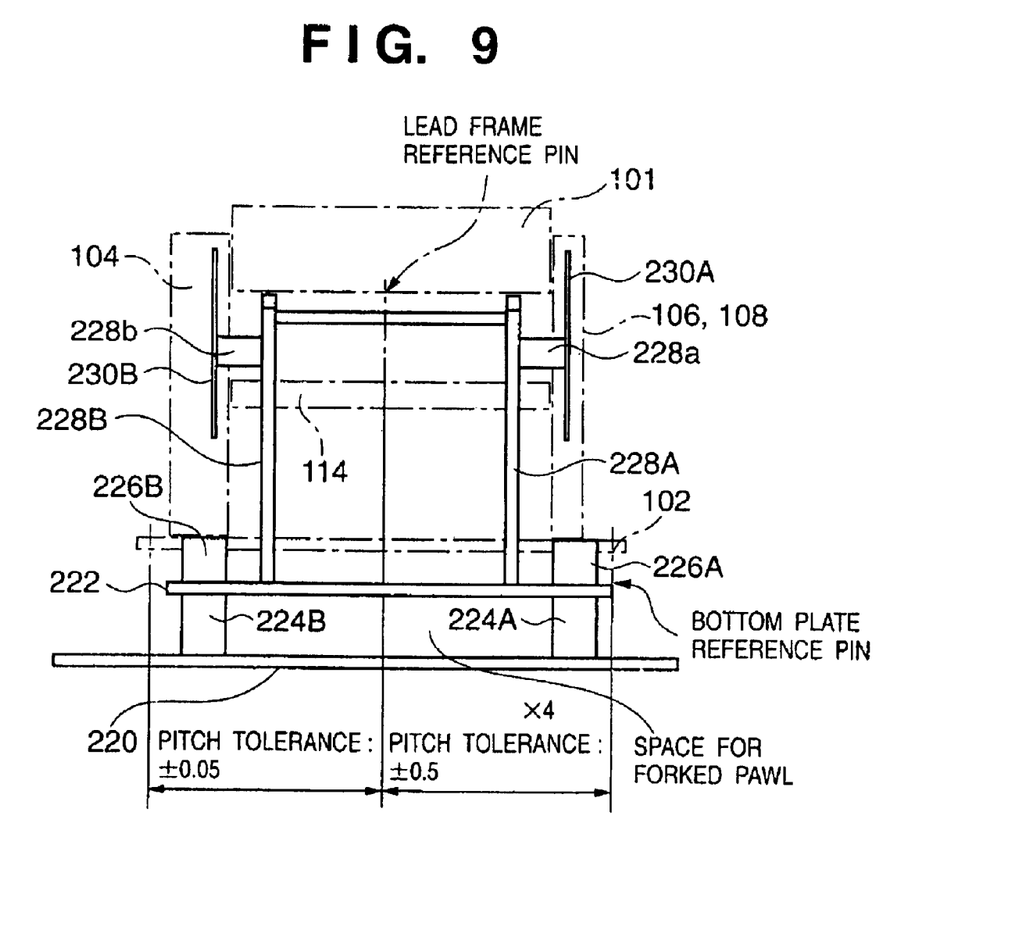
FIG. 9 is a view showing the arrangement of a welding jig used in laser welding operation for the image forming apparatus according to one embodiment.

FIG. 9 is a view showing the arrangement of a welding jig to be used in laser welding operation for the image forming apparatus according to this embodiment. The same reference numerals as those in the casing structure for the image forming apparatus described above denote the same members.

Referring to FIG. 9, reference numeral 220 denotes a jig base board; and 222, a holding member for the casing structure. The holding member 222 is set on the jig base board 220 through holders 224A and 224B. Bottom plate receiving members 226A and 226B are arranged at two ends on the holding member 222, and the bottom plate member 102 is placed on the receiving members 226A and 226B.

Reference numerals 228A and 228B respectively denote first and second frame receiving members fixed on the holding member 222. The frame member 101 is placed on the frame receiving members 228A and 228B. Retaining plate members 230A and 230B are attached to the first and second frame receiving members 228A and 228B through cross-beam members 228a and 228b, respectively. The retaining plate members 230A and 230B can be opened/closed like doors with respect to the cross-beam members 228a and 228b, respectively.

How the welding operation is performed by using the above jig will be described.

The bottom plate member 102 is placed on the holding member 222, and the frame member 101 is placed on the first and second frame receiving members 228A and 228B.

Subsequently, the rear plate member 104 is inserted between the bottom plate member 102 and frame member 101. The rear plate member 104 is urged against the bottom plate member 102 and frame member 101 in a stationary state with the retaining plate member 230A coupled to the first frame receiving member 228A.

Similarly, the right and left plate members 106 and 108 are urged in a stationary state with the retaining plate member 230B coupled to the second frame receiving member 228B. Furthermore, the stay members 110 and 112 are built in the resultant structure.

In this manner, the respective members that build the casing are maintained in the assembled state with the jig. The welding operation for the respective welded portions shown in FIG. 6 is performed with a laser welding machine (not shown).

As described above, the mechanical strength of the plurality of metal plates to be overlaid and welded is checked by measuring the length of the lower bead, so frequent alteration in welding conditions can be coped with.

As many apparently widely different embodiments of the present invention can be made without departing from the spirit and scope thereof, it is to be understood that the invention is not limited to the specific preferred embodiments described above thereof except as defined in the claims.

What is claimed is:

1. A casing structure formed by connecting a plurality of metal members by laser welding, comprising:

a board member; and a plate member to be coupled to said board member, wherein said board member and said plate member are partially overlapped and welded with a laser to form a line-like welded portion, and a ratio of a length of an upper bead of the welded portion along a longitudinal direction of the welded portion to a length of a lower bead of the welded portion along the longitudinal direction is set to not less than a predetermined value.

2. The casing structure according to claim 1, wherein the casing is used in an image forming apparatus, said board member is a frame member for placing an original table unit and an optical unit of the image forming apparatus thereon, said plate member is a member to be welded to the frame member, and the thicknesses of the frame member and of said plate member and a gap size of an overlaid portion of said frame member and said plate member are respectively set within predetermined ranges.

3. A casing structure formed by connecting a plurality of metal members by welding, comprising:

a first member; and a second member welded to said first member, wherein said first member and said second member are partially overlapped and welded to have a first bead welded portion on said first member and a second bead welded portion on said second member, with a ratio of a length of the first bead along a longitudinal direction of the welded portion to a length of the second bead along the longitudinal direction set to a predetermined value.

4. The casing structure according to claim 3, wherein the predetermined value is between approximately 1 and 2.

* * * * *

UNITED STATES PATENT AND TRADEMARK OFFICE
CERTIFICATE OF CORRECTION

| | | |
|---|---|---|
| PATENT NO. | : 6,786,101 B2 | Page 1 of 1 |
| APPLICATION NO. | : 10/159131 | |
| DATED | : September 7, 2004 | |
| INVENTOR(S) | : Koji Iwai et al. | |

It is certified that error appears in the above-identified patent and that said Letters Patent is hereby corrected as shown below:

<u>COLUMN 1</u>:

Line 44, "guaranteed for." should read --guaranteed.-- and "for." should be deleted.

<u>COLUMN 2</u>:

Line 9, "guaranteed for." should read --guaranteed.--.

<u>COLUMN 6</u>:

Line 2, "guaranteed for." should read --guaranteed.--.

<u>COLUMN 8</u>:

Line 51, "casing" should be deleted.
      Line 64, "casing" should be deleted.

Signed and Sealed this

Sixth Day of March, 2007

JON W. DUDAS
*Director of the United States Patent and Trademark Office*